United States Patent [19]

Gunther

[11] 4,199,575
[45] Apr. 22, 1980

[54] METHOD OF TREATING DERMATITIS VENENATA

[76] Inventor: Roland E. Gunther, R.D. 1, Box 282, New Berlin, N.Y. 13411

[21] Appl. No.: 38,409

[22] Filed: May 14, 1979

Related U.S. Application Data

[63] Continuation-in-part of Ser. No. 890,527, Mar. 27, 1978, abandoned.

[51] Int. Cl.$^2$ ............... A61K 31/09; A61K 31/66
[52] U.S. Cl. .................................. 424/217; 424/341
[58] Field of Search ........................... 424/341, 217

[56] References Cited

U.S. PATENT DOCUMENTS

| | | | |
|---|---|---|---|
| 2,857,311 | 10/1958 | Thurmon et al. | 424/79 |
| 3,749,772 | 7/1973 | Cardarelli et al. | 424/10 |
| 3,922,342 | 11/1975 | Rathbun | 424/79 |
| 4,002,737 | 1/1977 | Borris | 424/94 |
| 4,020,183 | 4/1977 | Asculai et al. | 424/341 |

*Primary Examiner*—Allen J. Robinson
*Attorney, Agent, or Firm*—Donald A. Kettlestrings

[57] ABSTRACT

A treatment for exposure to poison ivy and the like, in which the irritant principle is removed from the skin, mainly by dissolving it. The solvent is an innocuous surfactant that bears some structural similarity to the irritant, and for this reason can dissolve and displace the latter.

10 Claims, No Drawings

METHOD OF TREATING DERMATITIS VENENATA

BACKGROUND OF THE INVENTION

This application is a continuation-in-part of Application Ser. No. 890,527 filed Mar. 27, 1978, now abandoned.

1. Field of the Invention

This invention is classed by the intended action under the American Pharmaceutical Association's heading of Poison Ivy and Poison Oak Remedies, specifically as "topical prophylaxis".

2. Description of the Prior Art

The third edition of the Handbook of Non-prescription Drugs, published by the A.Ph.A., states in its chapter on this subject:

"In his extensive clinical studies on poison ivy dermatitis, Kligman has grouped the topical or external prophylactic measures into three types
1. removal of the antigen by washing with soap and water or with organic solvents
2. use of barrier creams
3. detoxicants (oxidizing and complexing agents which chemically inactivate the antigen)
Many workers have demonstrated that benefits derived from these attempts are dubious..." (H. C. Wormser, p 91).

This reference would appear to lead to the conclusion that in truth there is no real "prior art".

The type of treatment with which this invention is concerned falls roughly into type 1, aimed at removal of the irritant, but differs in that the primary removal process is carried out in the absence of water.

Dermatitis Venenata, caused by contact with a number of plants of the Anacardiaceae Family such as Poison Ivy, Poison Oak and Poison Sumac, is due to a class of toxic compounds known as "urushiols". These compounds are di-phenols (catechols) that also possess a side chain on the benzene ring. (This side-chain may vary in its degree of unsaturation and the intensity of irritation is usually proportionate to the unsaturation.) One thing stands out immediately; it is a large organic molecule. Such molecules normally are practically insoluble in water. From all past experience this is also the case with Urushiols. The old folk remedy of using "laundry soap" possibly provided what little relief it gave due to its excess causticity, a feature one would not wish to overdo lest the cure add to the irritation already present. The application of organic solvents would also understandably have drawbacks in spreading the irritant and helping it to permeate into the skin. The literature also indicates that the Urushiols appear to couple with sites on the skin so that organic solvents are unable to carry out the removal expected from their use.

SUMMARY OF THE INVENTION

The present invention is characterized by effectively removing Urushiols from the skin. It makes use of a class of surfactants that have structural similarity with portions of the irritant; they are phenol derivatives, also possessing alkyl side chains, that have been endowed with hydrophilicity by reaction with ethylene oxide. The class is known as alkyl aryl polyglycol ethers. They are available in essentially moisture-free state, which guarantees their ability to dissolve the Urushiols, and they are then capable of being efficiently washed off the skin after being used to pick up the irritant; rinsing of the surfactant however is only done after repeated applications and physical removals have been made in the complete absence of moisture to "wash" the skin of Urushiol.

DESCRIPTION OF THE PREFERRED EMBODIMENTS

When evidence of Dermatitis Venenata begins to appear, and contact with Poison Ivy or the like is suspected, the area is treated according to this invention as follows: a therapeutically-effective amount of a hydrophilic, moisture-free surfactant of the class of alkyl aryl polyglycol ethers sufficient to provide a coating of about ½ to one millimeter in thickness, e.g. about 0.05 to 0.1 ml per square centimeter of area to be treated, is dabbed upon the entire affected area. The surfactant is then wiped up with a tissue or a swab, always working toward the middle of the area in order to avoid spreading it. When the surfactant has been quite thoroughly removed, a fresh application is made and the procedure repeated. This procedure may be repeated any number of times, with three or four of such treatments being typical. The surfactant remaining on the skin is then washed off with copious amounts of water. If one wishes, the entire procedure including washing may be repeated, after first making sure that the area has been meticulously dried.

The ability of the alkyl aryl polyglycol ethers to pick up the Urushiols is based on a combination of factors. One stems from chemical similarity, which is based on both the Urushiols and the polyglycol ethers being derivatives of phenol and both having side chains. The similarity enhances the likelihood of mutual co-solvency. Another advantage that accrues from the similarity is the possibility that the surfactant may have the capability of displacing the irritant from the latter's attachment sites on the skin. The fact that the system is used under non-aqueous conditions is a definite benefit, and the case with which the very hydrophilic surfactant may finally be rinsed from the skin, carrying whatever residues of Urushiol it may still have picked up, is a final benefit.

As an example of a compound of the type found to be effective for use in carrying out the method of this invention, I cite the one known as Nonoxynol-9 and designated in the CTFA Cosmetic Ingredients Directory as being "the ethoxylated alkyl phenol that conforms generally to the formula $C_9H_{19}C_6H_4(OCH_2CH_2)_nOH$ where n has a average value of 9." The $C_9$ at the beginning of the above formula identifies it as a derivative of nonyl phenol. The latter is commercially readily available, so that the particular surfactants made from it enjoy widespread use. For the method of this invention, derivatives of other phenols may also be used, such as those having hexyl, heptyl, octyl, decyl or even longer side chains. Di-alkyl derivatives such as the one known as Nonyl Nonoxynol-9 are also useful. Derivatives of alkyl aryl polyglycol ethers such as their esters, may also be used: examples of these are the phosphate esters such as Nonoxynol 10 Phosphate.

Thus, alkyl aryl polyglycol ethers which are effective according to the present invention are compounds made by reacting the appropriate phenol with ethylene oxide and are characterized by the following formula:

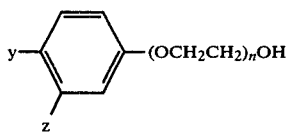

where
$y = C_m H_{2m=1}$,
$z = C_m H_{2m-1}$ or H
m being 6-10 and the average value of n is 4-150

The phosphate and sulfate ester derivatives of these compounds are also useful according to the invention. Most preferred of the polyglycol ethers and their ester derivatives of the invention are those when n−9 such as polyoxyethylene (9) hexyl phenyl ether, polyoxyethylene (9) heptyl phenyl ether, polyoxyethylene (9) octyl phenyl ether, polyoxyethylene (9) nonyl phenyl ether, and polyoxyethylene (9) decyl phenyl ether.

It should also be noted that mixtures of surfactants of the types named above are also effective, and where commercial syntheses produces combinations of such products, they may be used without first having to be resolved into distinct chemical entities.

It is evident that this treatment should be initiated as soon as possible after poison ivy or similar exposure is suspected. It has been found that the usual course of the reaction can be stopped up to the stage at which the skin has developed a shiny pebble-grained surface. When blisters have already formed, the service of a physician should be sought, as much to counter the risk of infection as to relieve the patient's distress.

A distinct advantage to this treatment lies in the fact that no harm can ensue should it be applied where actual exposure to the irritant has not really occurred. This class of surfactants has been in use for many years, in applications involving contact with skin and even mucous membranes, with great safety. Nonoxynol-9 is an ingredient of a number of vaginal preparations presently on the market, and can be judged therefrom to be especially innocuous. One caution is to be noted: these surfactants should not be allowed to get into the eyes.

It is claimed:

1. A method of treating Dermatitis Venenata on the skin of a patient, resulting from contact with Urushiols produced by plants of the family Anacardiaceae, which method comprises:
   A. applying to the affected area of said skin a therapeutically effective amount of a non-aqueous surfactant of the class of alkyl aryl polyglycol ethers having the formula:

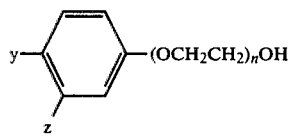

where
   $y = C_m H_{2m+1}$,
   $z = C_m H_{2m+1}$ or H, m being 6-10 and the average value of n is 4-150, or the phosphate or sulfate esters thereof,
   B. substantially physically removing said surfactant, and
   C. thoroughly rinsing the treated area with water.

2. The method of claim 1 wherein steps A and B are repeated at least once.

3. The method of claim 2 wherein steps A and B are repeated 3 or 4 times.

4. The method of claim 1 wherein said polyglycol ether is polyoxyethylene (9) nonyl phenyl ether.

5. The method of claim 1 wherein said surfactant is polyoxyethylene (9) dinonyl phenyl ether.

6. The method of claim 1 wherein said phosphate ester is polyoxyethylene (10) nonyl phenyl ether phosphate.

7. The method of claim 1 wherein said polyglycol ether is polyoxyethylene (9) hexyl phenyl ether.

8. The method of claim 1 wherein said polyglycol ether is polyoxyethylene (9) heptyl phenyl ether.

9. The method of claim 1 wherein said polyglycol ether is polyoxyethylene (9) octyl phenyl ether.

10. The method of claim 1 wherein said polyglycol ether is polyoxyethylene (9) decyl phenyl ether.

* * * * *